United States Patent
Makino et al.

(10) Patent No.: US 7,345,193 B2
(45) Date of Patent: Mar. 18, 2008

(54) METHOD OF CONTACT CATALYTIC REACTION

(75) Inventors: Kazuhiro Makino, Mie (JP); Hiroshi Iwasaka, Mie (JP); Kazuyuki Okubo, Mie (JP); Koji Hata, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/022,972

(22) Filed: Dec. 28, 2004

(65) Prior Publication Data

US 2005/0113600 A1 May 26, 2005

Related U.S. Application Data

(60) Division of application No. 10/412,578, filed on Apr. 14, 2003, now Pat. No. 6,914,156, which is a continuation of application No. PCT/JP01/08998, filed on Oct. 12, 2001.

(30) Foreign Application Priority Data

| Oct. 13, 2000 | (JP) | 2000-313366 |
| Oct. 30, 2000 | (JP) | 2000-330550 |
| Nov. 1, 2000 | (JP) | 2000-334137 |
| Nov. 20, 2000 | (JP) | 2000-352446 |

(51) Int. Cl.
*C07C 69/02* (2006.01)
*C07C 69/34* (2006.01)
*C07C 67/36* (2006.01)

(52) U.S. Cl. .......... 560/231; 560/201; 560/208
(58) Field of Classification Search ........ 422/219, 422/112, 110, 115, 295, 220, 311, 141, 143, 422/216

See application file for complete search history.

(56) References Cited

U.S. PATENT DOCUMENTS

| 4,121,039 A | 10/1978 | Parthasarathy et al. |
| 4,122,285 A | 10/1978 | Weitz et al. |
| 4,189,600 A | 2/1980 | Weitz et al. |
| 4,263,448 A * | 4/1981 | Leacock ............ 560/246 |
| 4,705,621 A * | 11/1987 | Penick ............. 208/146 |
| 5,302,357 A * | 4/1994 | Kramer et al. ...... 422/219 |

FOREIGN PATENT DOCUMENTS

| JP | 50-129514 | 10/1975 |
| JP | 2-53808 | 4/1977 |

OTHER PUBLICATIONS

Kirk-Othmer Encyclopedia of Chemical Technology Copyright 1999-2006 by John Wiley & Sons, Inc.*

* cited by examiner

*Primary Examiner*—Karl Puttlitz
(74) *Attorney, Agent, or Firm*—Oblon, Spivak, McClelland, Maier & Neustadt, P.C.

(57) ABSTRACT

A method of contact catalytic reaction by introducing a gas and a liquid into a lower part of a reaction zone comprising a liquid phase and a catalyst-packed bed held therein, where the catalyst-packed bed is a fixed bed.

17 Claims, 4 Drawing Sheets

METHOD OF CONTACT CATALYTIC REACTION

CONTINUING APPLICATION INFORMATION

This application is a Divisional of U.S. application Ser. No. 10/412,578, filed on Apr. 14, 2003 now U.S. Pat. No. 6,914,156, which is a Continuation of International Application No. PCT/JP01/08998, filed Oct. 12, 2001.

TECHNICAL FIELD

The present invention relates to a process for producing diacetoxybutene by reacting butadiene, acetic acid, and oxygen, and to others. Diacetoxybutene is an important compound as an intermediate for producing 1,4-butanediol or tetrahydrofuran.

BACKGROUND ART

The technique of reacting butadiene, acetic acid, and oxygen in the presence of a solid catalyst containing palladium to yield diacetoxybutene is known. Since the reaction proceeds in a liquid phase, it is important for efficiently carrying out the reaction to accelerate oxygen transfer from the gaseous phase to the liquid phase and thereby maintain a high oxygen concentration in the liquid phase.

Diacetoxybutene has hitherto been produced by a method of reaction in which a catalyst is disposed as a fixed bed in an oxygen-containing atmosphere and a liquid comprising butadiene and acetic acid is caused to flow down along the surface of the catalyst (see, for example, Japanese Patent Publication No. 42057/1980). This method of reaction, however, has the danger of generating an explosive mixed gas because the butadiene and acetic acid, which are liquid feed materials, partly vaporize and come into the oxygen-containing atmosphere, which is a continuous phase. Consequently, it has been necessary to regulate the oxygen concentration in the atmosphere so as to be lower than the lower explosion limit. It is a matter of course that low oxygen concentrations in the atmosphere constitute an obstacle to the acceleration of oxygen dissolution in the liquid.

In Japanese Patent Laid-Open No. 129514/1975 is disclosed a process for continuously producing diacetoxybutene which comprises feeding butadiene, acetic acid, and oxygen as upward cocurrent flows to a reactor in the presence of a fixed-bed catalyst comprising a supported palladium catalyst. However, this process, in which a gas containing oxygen is supplied to the liquid feed materials constituting a continuous phase, has the following drawbacks. The gas forms large bubbles and these bubbles are apt to coalesce with one another. Because of this, the area of the gas/liquid interface is apt to become small. Since the dissolution of oxygen in the feed liquid which is being fed to the fixed-bed catalyst is hence insufficient, the oxygen concentration in the liquid is insufficient, resulting in a reduced reaction efficiency. Furthermore, there is the danger of generating an explosive mixed gas because butadiene and acetic acid, which are liquid feed materials, partly vaporize and come into the bubbles. Consequently, as in the case of the method of reaction described above in which feed materials are caused to flow down, the oxygen concentration in the bubbles should be kept lower than the lower explosion limit and this is an obstacle to the acceleration of oxygen dissolution in the liquid.

A subject for the invention is to provide a method for efficiently reacting butadiene to produce diacetoxybutene in high yield, and to provide others.

DISCLOSURE OF THE INVENTION

The present inventors made intensive investigations in order to accomplish the subject described above. As a result, it has been found that when butadiene, acetic acid, and oxygen are fed to a reaction zone in which a solid catalyst containing palladium is present, the butadiene can be efficiently reacted and diacetoxybutene can be produced in high yield by introducing an oxygen-containing gas containing 7 mol % or more oxygen into a liquid phase comprising acetic acid and butadiene in such a manner that the gas forms fine bubbles.

It has also been found that by disposing, under the catalyst-packed bed, flow control plates projecting downward from the lower side of the bed, butadiene can be efficiently reacted and diacetoxybutene can be produced in high yield.

Furthermore, it has been found that regulating the catalyst-packed bed so as to have a porosity of from 0.30 to 0.41 is effective in efficiently reacting butadiene and producing diacetoxybutene in high yield.

The invention has been completed based on those findings.

Namely, the first essential point of the invention resides in a process for producing diacetoxybutene characterized in that in yielding diacetoxybutene by feeding butadiene, acetic acid, and oxygen in the presence of a solid catalyst containing palladium, an oxygen-containing gas containing 7 mol % or more oxygen is fed as fine bubbles to a reaction zone containing the solid catalyst.

The second essential point of the invention resides in a method of contact catalytic reaction comprising introducing a gas and a liquid into a lower part of a reaction zone comprising a liquid phase and a catalyst-packed bed held therein, passing the gas and liquid through the catalyst-packed bed as a flow of a gas/liquid mixed phase comprising the liquid and bubbles of the gas finely dispersed therein, and causing a gas and a liquid containing a reaction product to flow out of an upper part of the reaction zone, characterized in that the horizontal-direction movement of the gas/liquid mixed phase flow around the lower side of the catalyst-packed bed is controlled by disposing, under the catalyst-packed bed, flow control plates projecting downward from the lower side of the bed.

The third essential point of the invention resides in a method of contact catalytic reaction comprising introducing a gas and a liquid into a lower part of a reaction zone comprising a liquid phase and a catalyst-packed bed held therein, passing the gas and liquid through the catalyst-packed bed, and causing a gas and a liquid containing a reaction product to flow out of an upper part of the reaction zone, characterized in that the catalyst-packed bed is formed so as to have a porosity of from 0.30 to 0.41.

BEST MODE FOR CARRYING OUT THE INVENTION

Figure 1:
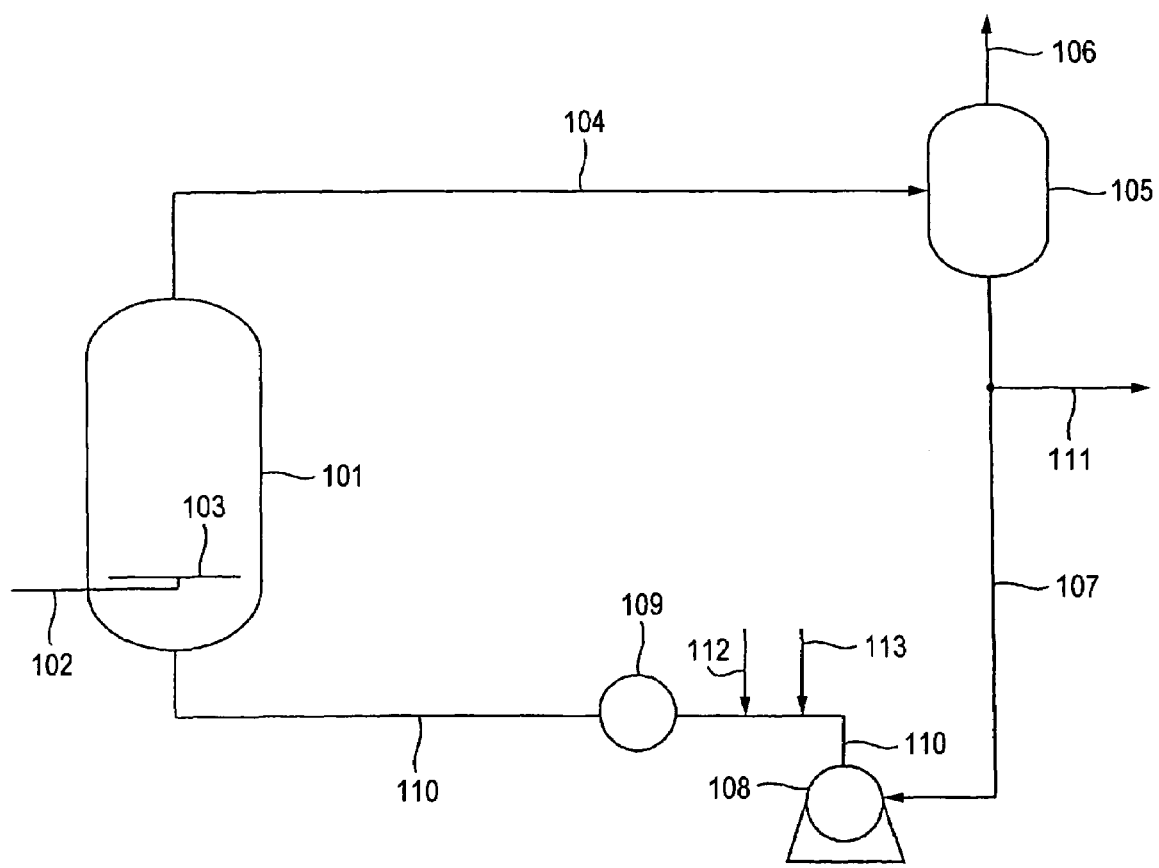
FIG. 1, FIG. 2, and FIG. 4 respectively illustrate flow sheet examples for practicing the invention.

First, an explanation will be made mainly on the first essential point of the invention.

The first essential point of the invention resides in a process for producing diacetoxybutene characterized in that in yielding diacetoxybutene by feeding butadiene, acetic acid, and oxygen in the presence of a solid catalyst containing palladium, an oxygen-containing gas containing 7 mol % or more oxygen is fed as fine bubbles to a reaction zone containing the solid catalyst.

In the invention, a zone in which the reaction product is yielded, e.g., a zone wherein a solid catalyst is present in a liquid phase comprising butadiene and acetic acid, is referred to as a reaction zone. Namely, the reaction zone as a whole is occupied by a liquid phase. An oxygen-containing gas is introduced into the liquid phase of the reaction zone so as to form fine bubbles, whereby diacetoxybutene is yielded.

The introduction of an oxygen-containing gas as fine bubbles into the liquid phase accelerates oxygen dissolution in the liquid phase. This is because fine bubbles have an exceedingly large surface area per unit volume and because the oxygen contained in the gaseous phase dissolves in the liquid phase through the interface between the two phases. The oxygen present in the oxygen-containing gas hence dissolves rapidly in the surrounding liquid phase. The diameter of the bubbles is generally 10 mm or smaller, preferably 5 mm or smaller, more preferably 3 mm or smaller, especially preferably 1 mm or smaller.

As a result of the acceleration of oxygen dissolution in the liquid phase, the oxygen concentration in the bubbles decrease rapidly and the formation of an explosive composition under reaction conditions is apt to be avoidable. Even when violent combustion occurs within part of the bubbles, this does not lead to an explosion such as in chain reactions because the energy of the combustion is low.

Furthermore, as long as the residence time of the bubbles in the reaction zone is adequate, the oxygen concentration in the bubbles decreases considerably and becomes sufficiently lower than the lower explosion composition limit before the bubbles leave the reaction zone.

Consequently, the introduction of an oxygen-containing gas as fine bubbles into the liquid phase makes it possible to use an oxygen-containing gas in which oxygen is present in a high concentration. The oxygen concentration of the oxygen-containing gas is generally 7 mol % or higher, preferably 12 mol % or higher. Examples of such an oxygen-containing gas include air diluted with a gas not participating in the reaction, such as nitrogen, and further include air, oxygen-enriched air, diluted oxygen gas, oxygen gas, and the like.

In a preferred embodiment of the invention, an oxygen-containing gas having such a high oxygen concentration as to form an explosive composition under the conditions employed in the reaction zone is fed to the reaction zone and the residence time of the bubbles in the reaction zone is regulated so that the bubbles at the outlet from the reaction zone has an oxygen concentration lower than the lower explosion composition limit.

Incidentally, when the reaction is conducted under ordinary conditions, i.e., under such conditions that the pressure is from 3 to 8 MPa, the temperature is from 60 to 120° C., and the liquid phase is mostly occupied by acetic acid, then the lower explosion composition limit can be estimated at a safety-side value using the following equation (1) or (2):

$$Y = -0.1\{(x/0.098)-1\}+12 \quad (1)$$

$$Y = -0.01\{(x/0.098)-1\}+6.6 \quad (2)$$

(wherein Y represents the lower limit of oxygen concentration (mol %) necessary for forming an explosive composition, and x represents the pressure (MPa) of the reaction zone; equation (1) is used when $x \leq 6$ MPa, and equation (2) is used when $6 < x \leq 8$ MPa). This estimated value may be used to determine the concentration of the oxygen-containing gas to be fed to the reaction zone and the concentration of the oxygen-containing gas to be caused to flow out of the reaction zone.

Techniques for introducing an oxygen-containing gas as fine bubbles into the liquid phase are not particularly limited. However, in the case of directly introducing an oxygen-containing gas into the reaction zone, it is preferred to feed the gas through two or more parts to the reaction zone with a sparger or the like so as to form fine bubbles.

It is also possible to disperse beforehand an oxygen-containing gas so as to form fine bubbles into the liquid phase to be fed to the reaction zone. For example, a preferred method is as follows. A liquid-circulating path for withdrawing the reaction liquid from the reaction zone and supplying the liquid to a lower part of the reaction zone is formed. Mixing devices are disposed in this circulating path in two-stage arrangement. An oxygen-containing gas is supplied to the former mixing device to disperse the gas as fine bubbles into the reaction liquid flowing through the circulating path. Subsequently, butadiene is supplied to the latter mixing device to mix the butadiene with the reaction liquid containing the oxygen-containing gas dispersed therein as fine bubbles.

The method described above in which an oxygen-containing gas and butadiene are mixed with the reaction liquid flowing through the circulating path and the resultant mixture is fed to the reaction zone is effective in preventing the reaction zone from having local unevenness of oxygen or butadiene concentration and in thereby enabling the reaction to proceed smoothly.

Examples of methods for mixing an oxygen-containing gas and butadiene with the reaction to liquid flowing through the circulating path include: a method in which an oxygen-containing gas and butadiene are simultaneously mixed; a method in which butadiene is mixed and an oxygen-containing gas is then mixed; a method in which an oxygen-containing gas is mixed first and butadiene is then mixed; and the like. However, the method in which an oxygen-containing gas is mixed first and butadiene is then mixed is preferred in that it can form fine bubbles without fail.

Any desired mixing devices may be disposed in the circulating path as long as the desired mixing effect is attained therewith. However, static mixers are preferred. As is well known, a static mixer is an in-line mixing device which is to be disposed in a piping and has no mechanical driving parts and in which a member called an element has been disposed inside in place of a mechanical part. When fluids such as liquids or gases pass through a static mixer, they undergo separation and inversion due to the element and mixing/dispersion thus proceeds. By the use of a static mixer, an oxygen-containing gas can be dispersed as fine bubbles having a diameter of preferably 3 mm or smaller, especially preferably 1 mm or smaller, into the reaction liquid passing through the circulating path. This effect is enhanced by regulating the ratio of the volume of the gas to that of the liquid to from 0.05 to 1.0.

In the case where a gas/liquid mixed phase flow comprising a reaction liquid and an oxygen containing gas finely dispersed therein is fed to a lower part of the reaction zone, it is preferred to feed the mixed phase through many nozzles disposed throughout the reaction zone so that the mixed phase is evenly fed to the whole reaction zone. The opening diameter of the nozzles and the number of the nozzles may be suitably determined according to the sectional area of the reaction zone into which the gas/liquid mixed phase flow is discharged from the nozzles.

The flow rate of the gas/liquid mixed phase discharged from the nozzles is usually 5 m/sec or lower, preferably from 0.5 to 3 m/sec. As long as the flow rate is within this range, the gas/liquid mixed phase flow can be diffused into the whole reaction zone with great ease, without raising difficulties in apparatus modification by enlarging the sectional area of all nozzle openings.

It is preferred to dispose a collision plate (baffle plate) above each nozzle so that the gas/liquid mixed phase flow discharged from the nozzle collides against it and thereby disperse in cross directions. The size of the collision plate is generally from 1 to 9 times the sectional area of the nozzle opening. Namely, in the case of an ordinary nozzle with a circular section, a disk of a size about from 1 to 3 times the diameter of the nozzle may be disposed concentrically above the nozzle.

Although the position in which the collision plate is to be disposed is suitably regulated according to the sectional area of the nozzle opening and the rate of discharge, it is generally preferably at from 5 to 30 cm above the nozzle outlet. Especially when the position of the collision plate is within this range, the movement of the gas/liquid mixed phase flow discharged is not inhibited and the cross-direction dispersion of the gas/liquid mixed flow is sufficient. In general, the larger the sectional area of the opening of the nozzle used, the more the regulation of the size and position of the collision plate is important. For disposing nozzles and collision plates as described above, it is generally preferred to pack the solid catalyst so as to form a catalyst-packed bed. In this case, the reaction, zone is in the catalyst-paced bed. Usually, the catalyst-packed bed has been fixed with a catalyst-supporting material.

After the gas/liquid mixed phase flow comprising a reaction liquid and an oxygen-containing as finely dispersed therein has ascended to around the lower side of the catalyst-packed bed, the gas/liquid mixed phase flow tends to partly flow in horizontal directions along the lower side of the catalyst-packed bed. Consequently, flow control plates projecting downward from the lower side of the catalyst-packed bed are disposed so as to prevent the gas/liquid mixed phase flow from moving in horizontal directions beyond these flow control plates. This is preferred for the efficient production of diacetoxybutene. Namely, the lower side of the bed is partitioned into many sections with the flow control plates so that the gas/liquid mixed phase flow which has flowed into each section enters the catalyst-packed bed through this section.

The flow control plates are preferably disposed so that the upper end of the plates is in contact with the lower side of the catalyst-packed bed or is located under the lower side of the catalyst-packed bed through a catalyst-supporting material. In the case where the flow control plates are disposed so that the upper end thereof is apart from the lower side of the catalyst-packed bed, the distance between the upper end of the flow control plates and the lower side of the catalyst-packed bed is generally preferably 20 mm or shorter from the standpoint of preventing the gas/liquid mixed phase flow from moving in horizontal directions. The catalyst-supporting material may have been united with the flow control plates.

Furthermore, the height of the flow control plates, i.e., the length over which the plates project downward, is generally 30 mm or more, preferably 100 mm or more. Although there is no particular upper limit on the height of the flow control plates, the height thereof is generally up to 30 cm. This range is especially preferred from the standpoint of enabling the gas/liquid mixed phase flow to evenly flow into the sections formed with the flow control plates.

Figure 5:
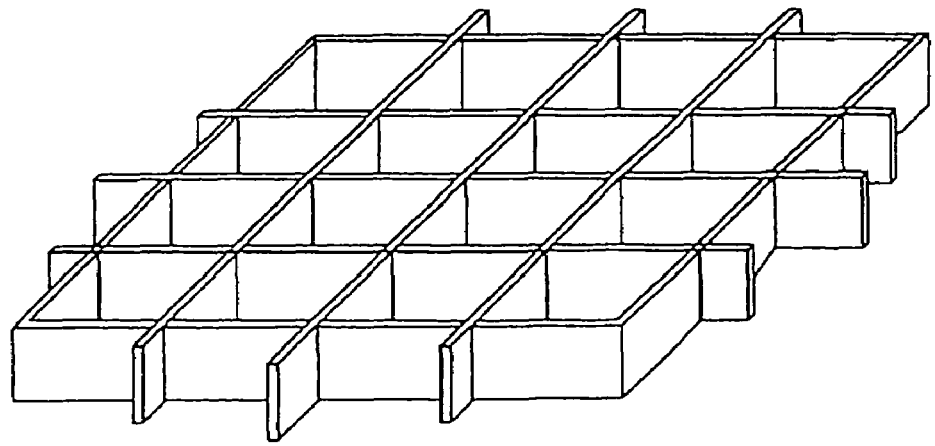
FIG. 5 is a view diagrammatically illustrating an example of flow control plates.

Although the number of sections to be formed with the flow control plates depends on the cross-sectional area of the catalyst-packed bed, it is preferably 10 or more. The size of each section is preferably 0.25 $m^2$ or smaller. For example, in the case of square sections, the length of each side is preferably 50 cm or smaller. Smaller section sizes are effective in enabling the gas/liquid mixed phase flow to evenly enter the catalyst-packed bed even when the bed has large local differences in flow resistance. There is no particular lower limit on the size of each section. However, when the catalyst-packed bed is an industrial-scale one, the size of each section is preferably $9 \times 10^{-4}$ $m^2$ or larger. For example, in square sections, the length of each side is preferably 3 cm or larger. FIG. 5 diagrammatically shows an example of the flow control plates.

The height-direction distance between the lower end of the flow control plates and the inlet for gas introduction into the reaction zone is preferably 20 cm or longer, more preferably 50 cm or longer, although it depends on methods of liquid and gas introduction into the reaction zone, the superficial velocities thereof, etc. The upper limit of that distance is preferably 3 m or shorter. By regulating that distance so as to be within this range, the gas/liquid mixed phase flow entering each section can be easily made even.

The effect of the flow control plates is significant in large catalyst-packed beds having a sectional area of 1 $m^2$ or larger, especially 3 $m^2$ or larger.

The catalyst to be used in the invention is one comprising a support and, having provided thereon, palladium and a promoter ingredient. As the support can be used an ordinary one such as, e.g., silica, alumina, silica-alumina, titania, or activated carbon. Examples of the promoter ingredient include tellurium, bismuth, antimony, selenium, copper, and the like. The palladium content of the supported palladium catalyst is preferably from 0.1 to 20% by weight. The content of the promoter ingredient, e.g., bismuth or selenium, therein is preferably from 0.01 to 30% by weight.

The catalyst may be in a spherical, solid cylinder, or hollow cylinder form or in the form of crushed particles, etc. However, a spherical or nearly spherical form is preferred. The size of the catalyst is preferably about from 1 to 6 mm. When the catalyst size is larger than 1 mm, the resistance of the passing of the gas/liquid mixed phase flow through the catalyst-packed bed is lower. On the other hand, catalyst sizes smaller than 6 mm result in a larger area of reaction sites per unit volume. The size of a catalyst is the arithmetic average of the longest diameter of a projected figure and the length of the longest one of the diameters perpendicular to that longest diameter. The catalyst is preferably packed so as to result in a packing density of 0.35 g/ml or higher. The packing density is determined by dividing the weight of the catalyst packed in the catalyst-packed bed by the volume of the catalyst-packed bed.

In the invention, a fixed bed is used as the catalyst-packed bed.

In the invention, the catalyst-packed bed is desirably formed so as to result in a porosity of generally from 0.30 to 0.41, preferably from 0.33 to 0.40. When the porosity is lower than 0.41, the catalyst particles are inhibited from readily flowing, whereby the friction among the catalyst particles is reduced accordingly and catalyst deterioration is reduced. When the porosity is higher than 0.30, catalyst packing is easier and the power cost can be prevented from increasing because the resistance of the passing of the gas/liquid mixed phase flow through the catalyst-packed bed is lower.

Apparatus for packing the catalyst are not particularly limited. For example, use may be made of those disclosed in U.S. Pat. Nos. 3,804,273 and 4,433,707, etc.

The porosity of a catalyst-packed bed is calculated using the following equation:

$$\text{Porosity of catalyst-packed bed} = 1 - Ax(1/B+C)$$

(wherein A indicates the packing density g/cm$^3$) of the catalyst; B indicates the true density (g/cm$^3$) of the catalyst; and C indicates the pore volume (ml/g) of the catalyst).

The true density of the catalyst can be calculated from the wt % of each component in the catalyst and the density thereof. The pore volume of the catalyst can be determined by the method of mercury penetration.

It is preferred in the invention that a catalyst-packed bed be formed so as to have a porosity of from 0.30 to 0.41 and a liquid and a gas be introduced into a lower part of the catalyst-packed bed and passed therethrough as an upward flow. The superficial velocity of each feed material is preferably in the range of from 0.05 to 10 cm/sec. In the case of producing diacetoxybutene from butadiene, acetic acid, and oxygen, the superficial velocity of an oxygen-containing gas is preferably in the range of from 0.05 to 10 cm/sec, and the superficial velocity of a liquid comprising butadiene and acetic acid is preferably in the range of from 1 to 20 times the superficial velocity of the oxygen-containing gas.

In the invention, the reaction can be conducted in an ordinary way. Usually, the reaction is performed at from 60 to 120° C. and from 3 to 8 MPa. Although the reaction may be conducted under conditions outside that range according to need, it is preferred to employ that range in view of reaction rate, side reactions, apparatus cost, etc. Since this reaction is an exothermic reaction, a large amount of acetic acid serving also as a solvent is cause to be present in the reaction zone in order to facilitate temperature regulation in the reaction zone. Furthermore, a liquid-circulating path may be formed for circulating the reaction liquid, and this circulating path may be provided with a cooling device. Preferably, the cooling device is disposed before the mixing device so that an oxygen-containing gas is mixed with and dispersed into the reaction liquid which has been cooled. It is also preferred that the acetic acid to be fed to the reaction zone be supplied, before the cooling device, to the reaction liquid which is flowing through the circulating path. In a preferred mode of reaction temperature regulation, the reaction products which are flowing out of the reaction zone are partly withdrawn from the system and subjected to a post-treatment step in which the diacetoxybutene yielded is recovered, and the remainder is cooled and circulated to the reaction zone.

Furthermore, the acetic acid and butadiene to be freshly fed are preferably mixed with the circulating flow before being fed to the reaction zone. The ratio (volume ratio) of the gaseous phase to the liquid phase to be introduced into the reaction zone, i.e., the sum of the circulating flow and the acetic acid and butadiene to be freshly fed, is preferably from 0.05 to 1.0. Although the acetic acid, butadiene, and oxygen-containing gas to be fed to the reaction zone are usually introduced as cocurrent flows into the reaction zone, they may be introduced as countercurrent flows into the reaction zone according to need.

An example of flow sheets for the production of diacetoxybutene by the process of the invention is shown in FIG. 1. In the figure, numeral 101 denotes a reactor, in which a solid catalyst containing palladium has been packed so as to form a fixed bed. For the purpose of avoiding drift, the catalyst bed is preferably formed in two or more layers perpendicular to the flow. Numeral 102 denotes a feed pipe for an oxygen-containing gas. The oxygen-containing gas fed is discharged as fine bubbles with a sparger 103 into a lower part of the reactor. The gaseous phase and liquid phase flowing out of the reactor are introduced through a piping 104 into a gas/liquid separator 105. The gaseous phase in the gas/liquid separator is discharged from the system through a piping 106. The liquid phase is discharged through a circulating piping 107 and introduced into a lower part of the reactor through a circulating pump 108, cooler 109, and piping 110. The liquid phase containing diacetoxybutene in an amount corresponding to the diacetoxybutene yielded in the reactor is withdrawn somewhere in the circulating piping 107 through a piping 111 and is sent to a post-treatment step for recovering diacetoxybutene. Somewhere in the piping 110, butadiene and acetic acid as feed materials are supplied through feed pipes 112 and 113, respectively. The butadiene and acetic acid may be supplied to the piping 110 after the cooler 109. Of the liquid phase withdrawn from the gas/liquid separator, the part which is discharged from the system through the piping 111 usually accounts for from 10 to 30% of the liquid phase, and the remainder, which accounts for from 90 to 70%, is circulated to the reaction zone. Namely, a large amount of the liquid phase is circulated through the reactor 101, gas/liquid separator 105, and cooler 109 and this circulating flow is used to regulate the temperature of the reactor 101 to be constant.

Figure 2:
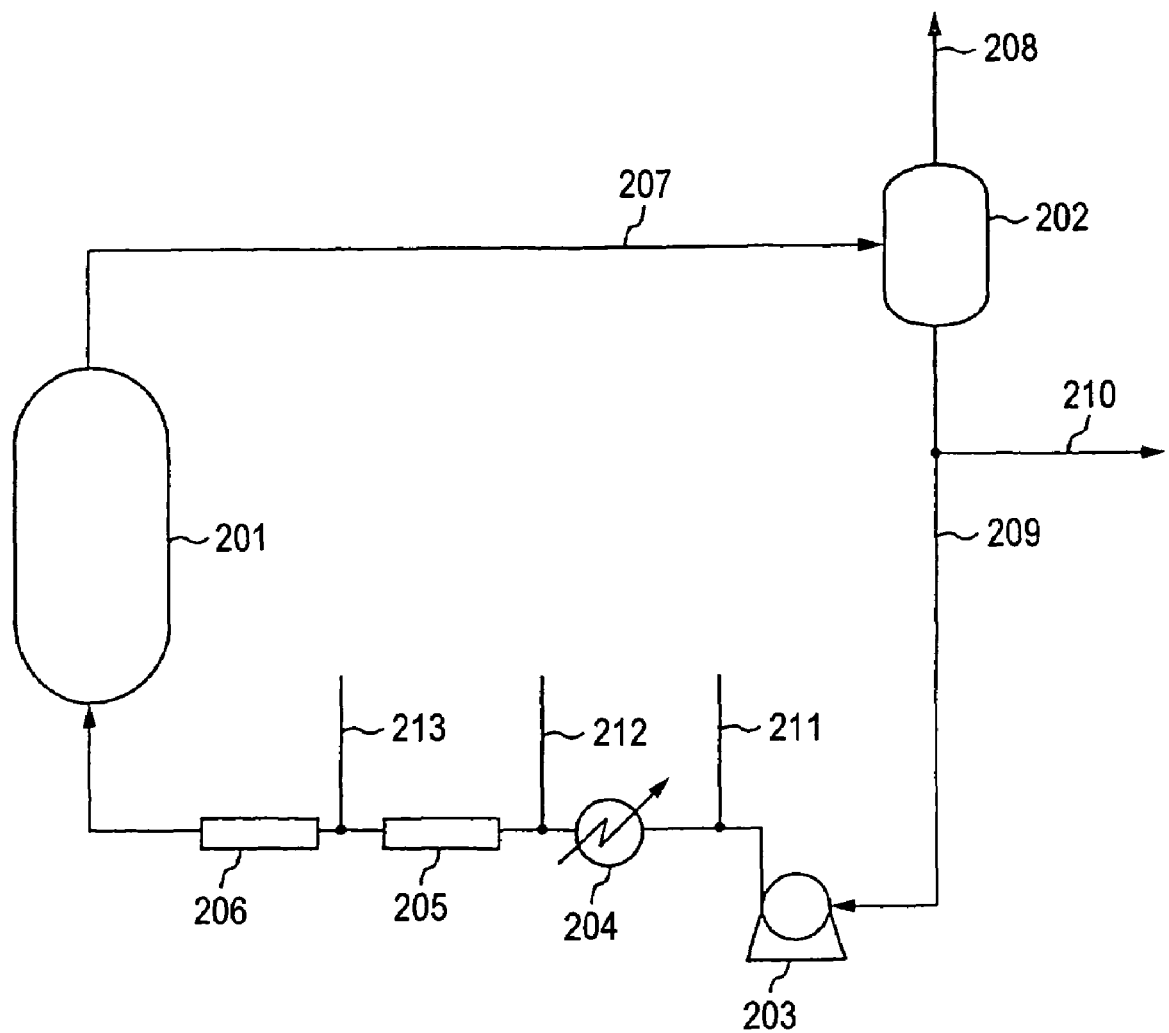

Another example of flow sheets for the production of diacetoxybutene by the process of the invention is shown in FIG. 2. In the figure, numeral 201 denotes a reactor, in which a solid catalyst containing palladium has been packed. The catalyst usually constitutes a fixed bed, and has been packed in two or more separate layers perpendicular to the direction of the flow for the purpose of avoiding drift. As the catalyst may be used an ordinary supported palladium catalyst. Namely, use may be made of one comprising a support such as silica, alumina, or activated carbon and, having provided thereon, palladium and a promoter such as bismuth, selenium, antimony, tellurium, copper, or the like. The palladium content of the supported palladium catalyst is preferably from 0.1 to 20% by weight, and the content of the promoter ingredient, e.g., bismuth or selenium, is preferably from 0.1 to 30% by weight.

Numeral 202 denotes a gas/liquid separator, into which the effluent from the reactor 201 flows through a piping 207. The gaseous phase is discharged from the system through the piping 208, and the liquid phase is withdrawn through a circulating piping 209. The liquid phase containing diacetoxybutene in an amount corresponding to the diacetoxybutene yielded by the reaction is withdrawn from the circulating piping 209 through a piping 210 and sent to a post-treatment step for recovering diacetoxybutene. Of the liquid phase withdrawn from the gas/liquid separator, the part which is discharged from the system through the piping 210 usually accounts for from 10 to 30% of the liquid phase, and the remainder, which accounts for from 90 to 70%, is supplied to a lower part of the reactor 201 through a pump 203, cooler 204, former mixing device 205, and latter mixing device 206. Namely, a large amount of a reaction liquid is flowing through the circulating piping 209. Acetic acid is supplied to this reaction liquid through a piping 211. Subsequently, an oxygen-containing gas is supplied through a piping 212, and the reaction liquid is supplied together with the oxygen-containing gas to former mixing device 205, where the gas is dispersed as fine bubbles into the reaction liquid. Butadiene is supplied to the resultant gas/liquid mixed phase flow through a piping 213. The butadiene is added to the reaction liquid, and these are supplied to the latter mixing device 206, evenly mixed, and fed to the reactor 201.

According to the invention, a high-concentration oxygen-containing gas can be used and oxygen can be rapidly dissolved in the liquid phase in the reaction zone. Because of this, the amount of butadiene which reacts per unit catalyst amount and unit time can be increased as compared with conventional techniques.

Next, an explanation will be made on the second essential point of the invention.

The second essential point of the invention resides in a method of contact catalytic reaction comprising introducing a gas and a liquid into a lower part of a reaction zone comprising a liquid phase and a catalyst-packed bed held therein, passing the gas and liquid through the catalyst-packed bed as a flow of a gas/liquid mixed phase comprising the liquid and bubbles of the gas finely dispersed therein, and causing a gas and a liquid containing a reaction product to flow out of an upper part of the reaction zone, characterized in that the horizontal-direction movement of the gas/liquid mixed phase flow around the lower side of the catalyst-packed bed is controlled by disposing, under the catalyst-packed bed, flow control plates projecting downward from the lower side of the bed.

In this invention, the flow control plates are as described above and can be applied to conventional gas/liquid mixed phase flows. They are applicable also to various reactions in which a gaseous starting material is reacted with a liquid starting material in the presence of a solid catalyst. Examples of such reactions include catalytic hydrogenation reactions such as the production of γ-butyrolactone or 1,4-butanediol by maleic anhydride hydrogenation, production of cyclohexane by benzene hydrogenation, production of alcohols by the hydrogenation of carboxylic acid esters, production of 1,6-hexanediol by adipic acid hydrogenation, and purification of crude terephthalic acid by hydrogenation. Preferred applications among these are the reactions using a supported noble-metal catalyst, such as, e.g., the production of 1,6-hexanediol by adipic acid hydrogenation or purification of crude terephthalic acid by hydrogenation.

Specifically, the flow control plates described above are effective in introducing a gas/liquid mixed phase flow into a reaction zone as in the case of, for example, mixing an oxygen-containing gas with a liquid feed material or reaction liquid and feeding the mixture to a reaction zone as explained with regard to the first essential point of the invention.

An explanation will then be given on the third essential point of the invention.

The third essential point of the invention resides in a method of contact catalytic reaction comprising introducing a gas and a liquid into a lower part of a reaction zone comprising a liquid phase and a catalyst-packed bed held therein, passing the gas and liquid through the catalyst-packed bed, and causing a gas and a liquid containing a reaction product to flow out of an upper part of the reaction zone, characterized in that the catalyst-paced bed is formed so as to have a porosity of from 0.30 to 0.41.

In this invention, the porosity of the catalyst-packed bed is as shown above. The porosity range of from 0.30 to 0.41 is applicable to various reactions heretofore in use in which a gaseous starting material is reacted with a liquid starting material in the presence of a solid catalyst. Examples of such reactions include catalytic hydrogenation reactions such as the production of γ-butyrolactone or 1,4-butanediol by maleic anhydride hydrogenation, production of cyclohexane by benzene hydrogenation, production of alcohols by the hydrogenation of carboxylic acid esters, production of 1,6-hexanediol by adipic acid hydrogenation, and purification of crude terephthalic acid by hydrogenation. Preferred applications among these are the reactions using the supported noble-metal catalyst, such as, e.g., the production of 1,6-hexanediol by adipic acid hydrogenation or purification of crude terephthalic acid by hydrogenation.

Specifically, regulating the porosity of the catalyst-packed bed to a value of from 0.30 to 0.41 as described above is effective in introducing a gas/liquid mixed phase flow into a reaction zone as in the case of, for example, mixing an oxygen-containing gas with a liquid feed material or reaction liquid and feeding the mixture to a reaction zone as explained with regard to the first essential point of the invention.

The invention will be explained below in more detail by reference to Examples, but the invention should not be construed as being limited to these Examples.

EXAMPLE 1

According to the flow sheet shown in FIG. 1, diacetoxybutene was produced from butadiene and acetic acid. A 5 wt % Pd-1.5 wt % Te/SiO$_2$ catalyst prepared by allowing silica to support palladium and tellurium was packed into a reactor so as to form a fixed bed. A circulating liquid containing freshly supplied butadiene and acetic acid was fed to a lower part of the reactor at 77° C. and 6 MPa, and air was fed through a sparger having a hole diameter of 3 mm at a flow rate of 20 m/sec so as to form fine bubbles. The amounts of the butadiene and acetic acid freshly fed were 0.223 kg/hr and 3.235 kg/hr, respectively, per kg of the catalyst. The amount of the air fed was 0.454 kg/hr per kg of the catalyst, and the amount of the circulating flow withdrawn from the gas/liquid separator and introduced into the reactor was 14.306 kg/hr per kg of the catalyst. The amount of the butadiene contained in this circulating flow and introduced into the reactor was 0.055 kg/hr per kg of the catalyst. The reaction was thus conducted continuously. As a result, the rate of reaction of the butadiene was 0.205 kg/hr per kg of the catalyst. The air bubbles fed through the sparger had a diameter of from 3 to 4 mm.

EXAMPLE 2

A reaction for yielding diacetoxybutene from butadiene and acetic acid was conducted in completely the same manner as in Example 1, except that oxygen-enriched air having an oxygen concentration of 25.0 mol % was used as an oxygen-containing gas. The rate of reaction of the butadiene was 0.213 kg/hr per kg of the catalyst.

COMPARATIVE EXAMPLE 1

Figure 3:
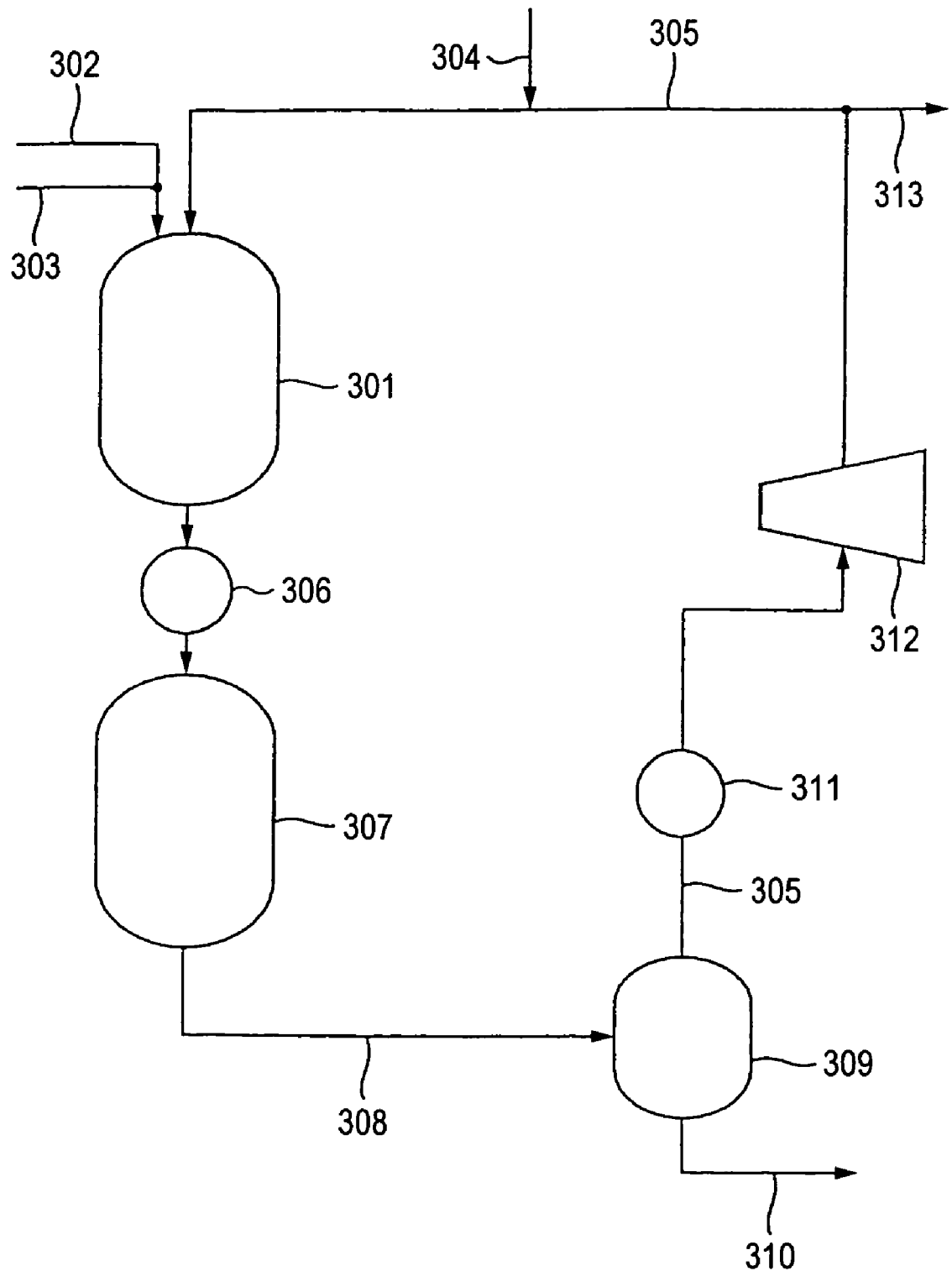
FIG. 3 illustrates a flow sheet example for a conventional technique.

Diacetoxybutene was yielded from butadiene and acetic acid by the gas circulation method shown in FIG. 3. In the figure, 301 denotes a first reactor packed with the same catalyst as used in Example 1. Butadiene and acetic acid to be freshly fed were fed to an upper part of the reactor 301 through pipings 302 and 303 At 77° C. and 6 MPa. Air was fed to the upper part of the reactor 301 through a piping 304 and a gas-circulating piping 305. The effluent from the reactor 301 was cooled to 77° C. with a cooler 306 and then fed to a second reactor 307 packed with the same catalyst as in the first reactor. The first reactor 301 and second reactor 307 each was of the type in which a liquid phase flowed down along the catalyst held in a gaseous atmosphere. The effluent from the second reactor was introduced into a gas/liquid separator 309 through a piping 308. The liquid phase was withdrawn from the system through a piping 310, and the gaseous phase was circulated to the reactor 301 through a piping 305. The piping 305 had a cooler 311 and compressor 312 disposed therein, and part of the circulating gas was withdrawn from the system through a piping 313. The amounts of the butadiene and acetic acid freshly fed were 0.187 kg/hr and 8.111 kg/hr, respectively, per kg of the catalyst. The amount of the air fed was 0.380 kg/hr per kg of the catalyst, and the amount of the circulating gas fed from the gas/liquid separator through a piping was 2.708 kg/hr per kg of the catalyst. The amount of the butadiene contained in this circulating gas and introduced into the reactors was 0.046 kg/hr per kg of the catalyst. The circulating gas which had been mixed with the air supplied through the piping 304 had an oxygen concentration of 5.6 mol %. The rate of reaction of the butadiene was 0.186 kg/hr per kg of the catalyst.

EXAMPLE 3

According to the flow sheet shown in FIG. 2, diacetoxybutene was produced from butadiene and acetic acid. A 5 wt % Pd-1.5 wt % Te/SiO$_2$ catalyst prepared by allowing silica to support palladium and tellurium was packed into a reactor so as to form a fixed bed. A static mixer was employed as each of the former and latter mixing devices disposed in the circulating piping. Air was used as an oxygen-containing gas. The amount of the reaction liquid fed to a lower part of the reactor through the circulating piping was 14.306 kg/hr per kg of the catalyst, and the amounts of the acetic acid, air, and butadiene mixed with the reaction liquid were 3.235 kg/hr, 0.454 kg/hr, and 0.223 kg/hr, respectively, per kg of the catalyst. The amount of the butadiene contained in the reaction liquid and introduced into the reactor was 0.055 kg/hr per kg of the catalyst. The gas/liquid mixed phase flow was fed through the circulating piping to the reactor with sixteen circular nozzles at a flow rate of 2 m/sec. A disk having a diameter 2.3 times the diameter of the nozzles was horizontally disposed at 20 cm above each nozzle concentrically with the nozzle. The gas/liquid mixed phase flow from each nozzle was caused to collide against the disk and disperse. The size of the bubbles of the gas/liquid mixed phase flow was 1 mm or smaller. This gas/liquid mixed phase flow was introduced into the reactor at 77° C. and 6 MPa. The reaction was continuously conducted under these conditions. As a result, the rate of reaction of the butadiene was 0.222 kg/hr per kg of the catalyst.

EXAMPLE 4

A 5 wt % Pd-1.5 wt % Te/SiO$_2$ catalyst prepared by allowing a silica support (product of Fuji Silysia Ltd.; CARiACT-17; spherical product with a diameter of 2.4-4 mm) to support palladium and tellurium through impregnation was introduced in an amount of 1,410 g into a cylindrical reactor having an inner diameter of 49.5 mm and a length of 2,000 mm through the upper opening thereof. The catalyst was densely packed by vibrating the reactor with a hammer. The packing density of the catalyst was 0.47 g/ml. The pore volume of the catalyst as measured by the method of mercury penetration was 0.87 ml/g, and the true density of the catalyst calculated from the components was 2.32 g/cm$^3$. Consequently, the porosity of the catalyst-packed bed was 0.39. A metal gauze was laid on the catalyst-packed bed, and zirconia spheres having a diameter of 10 mm were packed thereon so as to form a zirconia sphere layer having a height of 180 mm.

The reactor was maintained at 6 MPa, and 70° C. acetic acid containing butadiene and 70° C. nitrogen gas containing oxygen were continuously introduced into a lower part of the reactor at superficial velocities of 1.8 cm/sec and 1.5 cm/sec, respectively, and passed through the catalyst-packed bed upward. The nitrogen gas containing oxygen was introduced with a sparger so as to form fine bubbles. The liquid and gas introduction was thus continued over 2,700 hours to conduct a reaction for yielding diacetoxybutene. Thereafter, the catalyst was withdrawn through the upper part of the reactor and examined for palladium content. As a result, the palladium content had not decreased at all. Furthermore, the surface of the catalyst withdrawn was examined with an optical microscope (magnification, 50 diameters). As a result, almost no mars formed by friction were observed.

EXAMPLE 5

The same reactor as used in Example 4 was filled with water. This reactor was packed with 1,410 g of the same 5.2 wt % Pd-1.5 wt % Te/SiO$_2$ catalyst as used in Example 4, which had been prepared by allowing a silica support to support palladium and tellurium, to form a catalyst-packed bed. The catalyst had a packing density of 0.44 g/ml and a porosity of 0.43. A metal gauze was laid on the catalyst-packed bed, and zirconia spheres having a diameter of 10 mm were packed thereon so as to form a zirconia sphere layer having a height of 180 mm.

Acetic acid containing butadiene and nitrogen gas containing oxygen were continuously introduced into the reactor over 2,700 hours in completely the same manner as in Example 4 to conduct a reaction for yielding diacetoxybutene. Subsequently, the catalyst was withdrawn through the upper part of the reactor and examined for palladium content. As a result, the palladium content was found to be 4.8% by weight, i.e., it had decreased to 92.3% of the initial content. Furthermore, the surface of the catalyst withdrawn was examined with an optical microscope. As a result, many mars formed by friction were observed.

REFERENCE EXAMPLE 1

Example of Catalytic Activity Test

A reaction tube having an inner diameter of about 12 mm (sectional area, 1.005 cm$^2$) was packed with 4 g of a catalyst and maintained at 6 MPa and 80° C. Butadiene, acetic acid, and nitrogen gas containing 6 mol % oxygen were continuously introduced upward into the reaction tube from its bottom at rates of 0.15 mol/hr, 2.5 mol/hr, and 100 NL/hr, respectively, to yield diacetoxybutene. A reaction liquid obtained in the period from 4 hours after initiation of the reaction to 5 hours after the initiation and a reaction liquid obtained in the period from 6 hours after the initiation to 7 hours after the initiation were analyzed by gas chromatography. The rate of consumption (mmol/hr) of the butadiene per kg of the catalyst was calculated from the average of those found values and taken as catalytic activity. The results obtained are shown in Table 1.

TABLE 1

| Catalyst | Catalytic activity |
|---|---|
| A | 8810 |
| B | 8760 |
| C | 8640 |
| D | 7700 |

In the table, A is the same catalyst as used in Example 4; B is the catalyst withdrawn from the catalyst-packed bed after 2,700 hours in Example 4; C is the same catalyst as used in Example 5; and D is the catalyst withdrawn from the catalyst-packed bed after 2,700 hours in Example 5.

The catalyst used in Example 4 had suffered almost no frictional damage and, hence, underwent a decrease in catalytic activity as small as 0.6% even through the 2,700-hour reaction. In contrast, in the catalyst used in Example 5, the surface palladium had partly shed off due to frictional damage. Because of this, the catalyst used in Example 5 underwent a decrease in catalytic activity of 10.9% through the 2,700-hour reaction.

EXAMPLE 6

Figure 4:
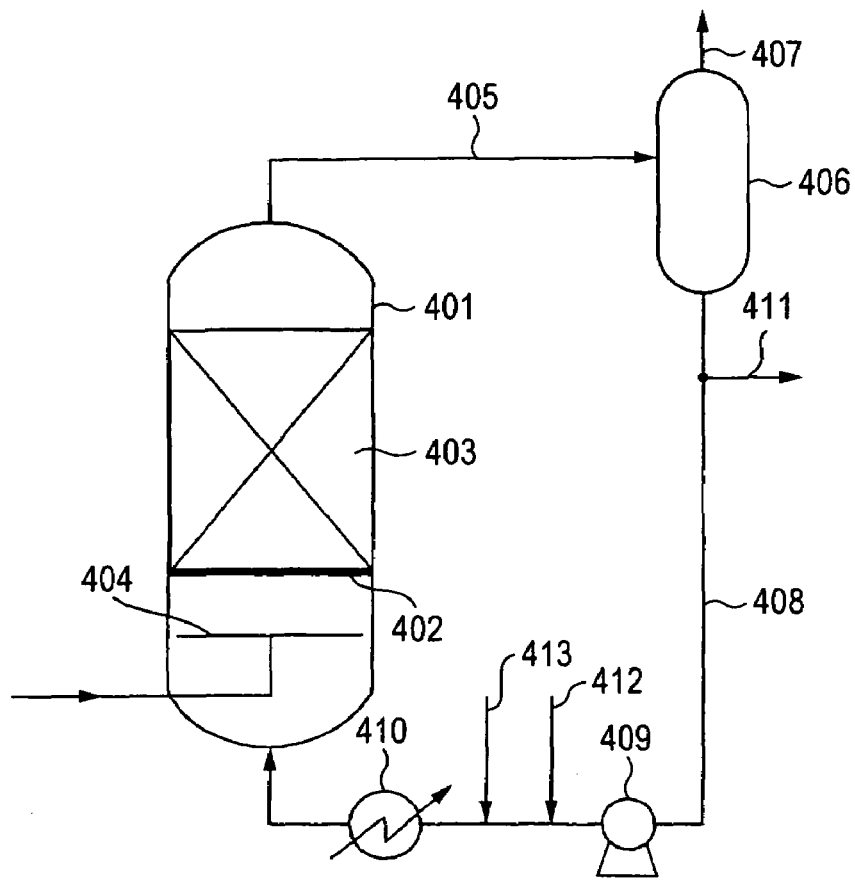

According to the flow sheet shown in FIG. 4, butadiene, acetic acid, and an oxygen-containing gas are reacted to produce diacetoxybutene. In the figure, 401 denotes a reactor. The reactor has a catalyst-packed bed 403 on a catalyst-supporting material 402 made of a metal gauze. The catalyst is a 5.0 wt % Pd-1.5 wt % Te/$SiO_2$ catalyst prepared by allowing a silica support to support palladium and tellurium through impregnation. Partition plates (flow control plates) having a height of 20 cm are arranged at right angles on the lower side of the catalyst-supporting material so as to partition the lower side into many squares of 20 cm×20 cm. Numeral 404 denotes a sparger for the oxygen-containing gas. The distance between the gas outlets of the sparger and the lower end of the partition plates is 120 cm. A gas/liquid mixed phase flow from the reactor is introduced into a gas/liquid separator 406 through a piping 405. The gaseous phase is withdrawn from the system through a piping 407. The liquid-phase is circulated to a lower part of the reactor 401 through a circulating piping 408 having a circulating pump 409 and cooler 410 disposed therein. A reaction liquid containing diacetoxybutene in an amount corresponding to the diacetoxybutene yielded by the reaction is withdrawn somewhere in the circulating piping through a piping 411 and sent to a product-treating system. Butadiene and acetic acid were supplied to the circulating piping through a piping 412 and a piping 413, respectively.

The reactor is maintained at 6 MPa, and a circulating reaction liquid, butadiene, acetic acid, and air are continuously fed thereto to continuously yield diacetoxybutene. The temperature of the circulating reaction liquid being fed is 77° C. The amounts of the circulating reaction liquid, butadiene, acetic acid, and air fed per kg of the catalyst are 14.3 kg/hr, 0.223 kg/hr, 3.24 kg/hr, and 0.454 kg/hr, respectively. The amount of butadiene in the circulating reaction liquid is 0.055 kg/hr per kg of the catalyst. The feed materials were reacted under these conditions. As a result, the rate of reaction of the butadiene was 0.211 kg/hr per kg of the catalyst.

While the invention has been described in detail and with reference to specific embodiments thereof, it will be apparent to one skilled in the art that various changes and modifications can be made therein without departing from the spirit and scope thereof.

This application is based on a Japanese patent application filed on Oct. 13, 2000 (Patent Application No. 2000-313366), Japanese patent application filed on October 30, 2000 (Patent Application No. 2000-330550), Japanese patent application filed on Nov. 1, 2000 (Patent Application No. 2000-334137), and Japanese patent application filed on Nov. 20, 2000 (Patent Application No. 2000-352446), the contents thereof being hereby incorporated by reference.

INDUSTRIAL APPLICABILITY

The invention relates to a process for producing diacetoxybutene, which is an important compound as an intermediate for producing 1,4-butanediol or tetrahydrofuran, by reacting butadiene, acetic acid, and oxygen, and according to the process it is possible to efficiently react butadiene to produce diacetoxybutene in high yield.

The invention claimed is:

1. A method of contact catalytic reaction for producing diacetoxybutene, comprising introducing an oxygen-containing gas and a liquid containing butadiene and acetic acid into a lower part of a reaction zone comprising a liquid phase and a catalyst-packed bed held therein, passing the gas and the liquid through the catalyst-packed bed as a flow of a gas/liquid mixed phase comprising the liquid and bubbles of the gas finely dispersed therein, and causing a gas and a liquid containing diacetoxybutene to flow out of an upper part of the reaction zone, wherein the horizontal-direction movement of the gas/liquid mixed phase flow around the lower side of the catalyst-packed bed is controlled by disposing, under the catalyst-packed bed, flow control plates projecting downward from the lower side of the bed, wherein the catalyst-packed bed is a fixed bed, wherein
the oxygen-containing gas contains 12 mol % or more of oxygen, and
the catalyst-packed bed has a porosity of from 0.30 to 0.41.

2. The process of claim 1, wherein the solid catalyst is one provided on the surface of a support selected from the group consisting of silica, alumina, silica-alumina, titania, and activated carbon.

3. The process of claim 1, wherein the flow control plates are disposed so as to partition the lower side of the catalyst-packed bed into ten or more sections.

4. The process of claim 1, wherein the flow control plates are disposed so as to partition the lower side of the catalyst-packed bed into sections of 0.25 $m^2$ or smaller.

5. The process of claim 1, wherein the flow control plates project over a length of 30 mm or longer.

6. The process of claim 1, wherein the height-direction distance between an inlet for gas introduction into the reaction zone and the lower end of the flow control plates is 20 cm or longer.

7. The process of claim 1, wherein a liquid-circulating path for withdrawing a reaction liquid from the reaction zone and supplying the liquid to a lower part of the reaction zone is formed and mixing devices are disposed in this circulating path in two-stage arrangement, and that the former mixing device is used to feed an oxygen-containing gas and disperse the gas into the reaction liquid flowing through the circulating path and butadiene is supplied to the latter mixing device and mixed with the reaction liquid.

8. The process of claim 7, wherein the mixing devices are static mixers.

9. The process of claim 1, wherein the catalyst has a particle diameter of from 1 to 6 mm and the packing density of the catalyst is 0.35 g/ml or higher.

10. The process of claim 1, wherein the gas which is being introduced into the reaction zone has a superficial velocity of from 0.05 to 10 cm/sec.

11. The process of claim 1, wherein the oxygen-containing gas is air.

12. The process of claim 1, wherein the oxygen-containing gas is oxygen-enriched air.

13. The process of claim 1, wherein the oxygen-containing gas is oxygen.

14. The process of claim 1, wherein the oxygen-containing gas is diluted oxygen gas.

15. The process of claim 1, which is conducted at a pressure of 3 to 8 MPa and a temperature of from 60 to 120° C.

16. The process of claim 1, wherein the catalyst-packed bed has a porosity of from 0.33 to 0.40.

17. The process of claim 1, wherein the ratio of the gaseous phase to the liquid phase to be introduced into the reaction zone is from 0.5 to 1.0.

* * * * *